(12) United States Patent
Detering et al.

(10) Patent No.: US 6,187,226 B1
(45) Date of Patent: Feb. 13, 2001

(54) THERMAL DEVICE AND METHOD FOR PRODUCTION OF CARBON MONOXIDE AND HYDROGEN BY THERMAL DISSOCIATION OF HYDROCARBON GASES

(75) Inventors: Brent A. Detering; Peter C. Kong, both of Idaho Falls, ID (US)

(73) Assignee: Bechtel BWXT Idaho, LLC, Idaho Falls, ID (US)

(*) Notice: Under 35 U.S.C. 154(b), the term of this patent shall be extended for 0 days.

This patent is subject to a terminal disclaimer.

(21) Appl. No.: 09/320,784

(22) Filed: May 27, 1999

Related U.S. Application Data

(63) Continuation-in-part of application No. 09/076,922, filed on May 12, 1998, now Pat. No. 5,935,293, which is a continuation-in-part of application No. 08/404,395, filed on Mar. 14, 1995, now Pat. No. 5,749,937.

(51) Int. Cl.[7] .............................. C07C 1/02; C01B 31/18; C01B 31/20; C01B 5/00
(52) U.S. Cl. .................. 252/373; 423/418.2; 423/437.1; 423/580.1
(58) Field of Search ................ 252/373; 423/418.2, 423/437.1, 580.1

(56) References Cited

U.S. PATENT DOCUMENTS

| 4,182,746 | 1/1980 | Myint ........................ 423/415 A |
| 4,844,437 | 7/1989 | Heck et al. ..................... 252/373 |
| 5,017,196 | * 5/1991 | Dewitz ........................... 48/210 |
| 5,486,313 | 1/1996 | De Jong et al. ................. 252/373 |
| 5,538,706 | 7/1996 | Kapoor et al. ................. 423/418.2 |
| 5,582,927 | 12/1996 | Andricacos et al. ............ 428/694 T |
| 5,723,505 | 3/1998 | Chaumette et al. .............. 518/702 |
| 5,733,941 | 3/1998 | Waycuilis ....................... 518/703 |
| 5,749,937 | 5/1998 | Detering et al. ................ 75/10.19 |
| 5,861,441 | 1/1999 | Waycuilis ....................... 518/703 |
| 5,883,138 | 3/1999 | Hershkowitz et al. ............ 518/703 |
| 5,886,056 | 3/1999 | Hershkowitz et al. ............ 518/703 |

* cited by examiner

Primary Examiner—Steven P. Griffin
Assistant Examiner—Jonas N. Strickland
(74) Attorney, Agent, or Firm—Workman Nydegger & Seeley

(57) ABSTRACT

Carbon monoxide is produced in a fast quench reactor. The production of carbon monoxide includes injecting carbon dioxide and some air into a reactor chamber having a high temperature at its inlet and a rapidly expanding a reactant stream, such as a restrictive convergent-divergent nozzle at its outlet end. Carbon dioxide and other reactants such as methane and other low molecular weight hydrocarbons are injected into the reactor chamber. Other gas may be added at different stages in the process to form a desired end product and prevent back reactions. The resulting heated gaseous stream is then rapidly cooled by expansion of the gaseous stream.

23 Claims, 10 Drawing Sheets

THERMAL DEVICE AND METHOD FOR PRODUCTION OF CARBON MONOXIDE AND HYDROGEN BY THERMAL DISSOCIATION OF HYDROCARBON GASES

RELATED APPLICATION

This application is a continuation-in-part of application Ser. No. 09/076,922, filed May 12, 1998, now U.S. Pat. No. 5,935,293 which is a continuation-in-part of application Ser. No. 08/404,395 filed Mar. 14, 1995, now U.S. Pat. No. 5,749,937 the disclosures of which are incorporated herein by reference.

CONTRACTUAL ORIGIN OF THE INVENTION

The United States Government has rights in this invention pursuant to Contract No. DE-AC07-94ID13223 between the United States Department of Energy and Lockheed Martin Idaho Technologies Company.

TECHNICAL FIELD

This present invention relates to equipment for thermal conversion of a source of carbon atoms and a source of oxygen atoms and other reactants such as methane to desired end products, particularly carbon monoxide and hydrogen. The end products may be either a gas or ultrafine solid particles. It also relates specifically to methods for effectively producing such end products.

BACKGROUND OF THE INVENTION

Carbon dioxide is a generally inert gas that is produced in abundance by combustion processes. Whether it is slash and burn deforesting that occurs in developing countries or it is the numerous combustion processes of industrialized nations, carbon dioxide is constantly being produced. Carbon dioxide is also often found in natural gas. As a natural gas component, carbon dioxide is a contaminant that lowers the burn efficiency of the natural gas. Natural gases that are being extracted from the North Slopes of Alaska may contain up to 20% carbon dioxide or more. At any amount, carbon dioxide acts as a contaminant for specific volume energy output. Additionally, in petroleum refining operations, natural gas is often flared and carbon dioxide is present in abundance in the combustion products.

If carbon dioxide could be used more efficiently, it could be converted to valuable feed stocks such as carbon monoxide. Carbon monoxide is also considered one of the primary culprits in global warming theory. As such, if carbon monoxide emissions were reduced in all processes where it is a product, the global warming rate would be affected.

Carbon monoxide is a valuable intermediate for many industries. The prior technology for production of carbon monoxide involved steam and/or catalytic reforming of natural gas to form the products of carbon monoxide and diatomic hydrogen.

It would be an improvement in the art to utilize the abundant carbon dioxide, that is produced by the large number of operations around the globe, to generate the valuable intermediate of carbon monoxide.

SUMMARY OF THE INVENTION

The present invention relates to the formation of carbon monoxide and hydrogen from feed stocks containing carbon, oxygen, and simple hydrocarbons such as methane. The present invention also relates to an integrated liquid natural gas reforming and hydrogen combustion process in which carbon monoxide and diatomic hydrogen are produced.

The inventive process operates by injecting carbon dioxide and other optional reactants into the inlet end of a reactor chamber and rapidly heating the reactants to produce a hot carbon monoxide product stream which flows toward the outlet end of the reactor chamber. The reactor chamber may have a predetermined length that is sufficient to allow heating of the reactant stream to a selected equilibrium temperature and a preferred equilibrium composition of primarily carbon monoxide and diatomic hydrogen.

Upon reaching the selected equilibrium temperature, the desired end product is available within the product stream as a thermodynamically stable or unstable reaction product at a location adjacent to the outlet end of the reaction chamber. The gaseous stream is passed through a restrictive convergent-divergent nozzle arranged coaxially within the remaining end of the reactor chamber to rapidly cool the gaseous stream by converting thermal energy to kinetic energy as a result of substantially adiabatic and isentropic expansion as it flows axially through the nozzle to minimize back reactions. Thereby the desired end product within the flowing gaseous stream is retained. Subsequently, the product stream is cooled and slowed down in velocity.

Preferably the rapid heating step is accomplished by introducing a stream of plasma arc gas to a plasma torch at the inlet end of the reactor chamber to produce a plasma within the reactor chamber which extends toward its outlet end.

An alternate method of this invention uses a virtual convergent-divergent nozzle. This is accomplished by directing one or more streams of particles, droplets, liquid, or gas into the main flow stream of the reaction chamber such that the main reactant flow stream is forced to flow as though a real convergent-divergent nozzle were present. This phenomena occurs because the reduced axial momentum of the directing flow effectively impedes the flow of the main stream, thereby forcing the majority of the main stream to flow around the impeding stream, similar to the flow through the restriction of a conventional converging-diverging nozzle. A similar cooling effect is achieved with the virtual nozzle. The directing or impeding stream(s) can play other roles than merely providing the virtual nozzle effect. In addition to keeping the main flow stream away from the wall, they can interact with the main stream further downstream in various ways to provide, for example, enhanced heat transfer, mixing, chemical reaction, etc. The virtual nozzle effect can also be utilized in combination with a conventional converging-diverging nozzle to achieve optimal performance. To obtain the desired expansion and cooling it will be necessary to adjust the velocity of the reactants, the quantity of the reactants, the number and position of the supply inlets, and diameter of the reaction chamber.

The present invention converts a predominantly carbon dioxide stream to carbon monoxide with minor amounts of impurities. The present invention also converts a carbon dioxide-rich hydrocarbon stream into carbon monoxide, diatomic hydrogen, and minor impurities including elemental carbon.

The present invention also relates to an on-board plasma quench reformer system for hydrocarbon fuel such as a natural gas fuel. In the on-board plasma quench reformer, either liquid natural gas or compressed natural gas is vaporized and converted into hydrogen and a selection of carbon compounds including carbon dioxide, carbon monoxide, and elemental carbon. At least the hydrogen is then supplied to the internal combustion engine as a reformed fuel source.

These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present reactor and method are directed toward high temperature reactions that decompose sources of carbon and oxygen as well as hydrocarbons such as methane into thermodynamically stable compounds of carbon monoxide and diatomic hydrogen, with minor impurities. The process requires rapid cooling to freeze the reaction products to prevent back reactions or decompositions to undesirable products. The process uses substantially adiabatic and isentropic expansion of gases in a converging-diverging nozzle for rapid quenching. This expansion can result in cooling rates exceeding $10^{10}$ K/s, thus preserving reaction products that are in equilibrium only at high temperatures.

The fast quench reactor and method of operation described in this disclosure take advantage of the temperatures in the range from about 500 to about 20,000° C. available in a high temperature heating means such as a thermal plasma to produce materials that are thermodynamically stable at these high temperatures. These materials include carbon dioxide and hydrocarbons.

A converging-diverging (De Laval) nozzle located downstream from the plasma and reactant addition inlet(s) produces a rapid drop in kinetic temperature in a flowing gas stream. This effectively "freezes" or stops all chemical reactions. It permits efficient collection of desired end products as the gases are rapidly cooled without achieving an equilibrium condition. Resulting end products which have been produced in the plasma at high temperature but are thermodynamically unstable or unavailable at lower temperatures can then be collected due to resulting phase changes (gas to solid) or stabilization by cooling to a lower equilibrium state (gas to gas).

The fast quench reactor and method of this invention shall be described and illustrated forthwith in terms of a rapid heating means comprising a plasma torch and a stream of plasma arc gas. However, it will be recognized that the rapid heating means can also include other rapid heating means such as lasers, and flames produced by oxidation of a suitable fuel, e.g. an oxygen/hydrogen flame.

Figure 1:
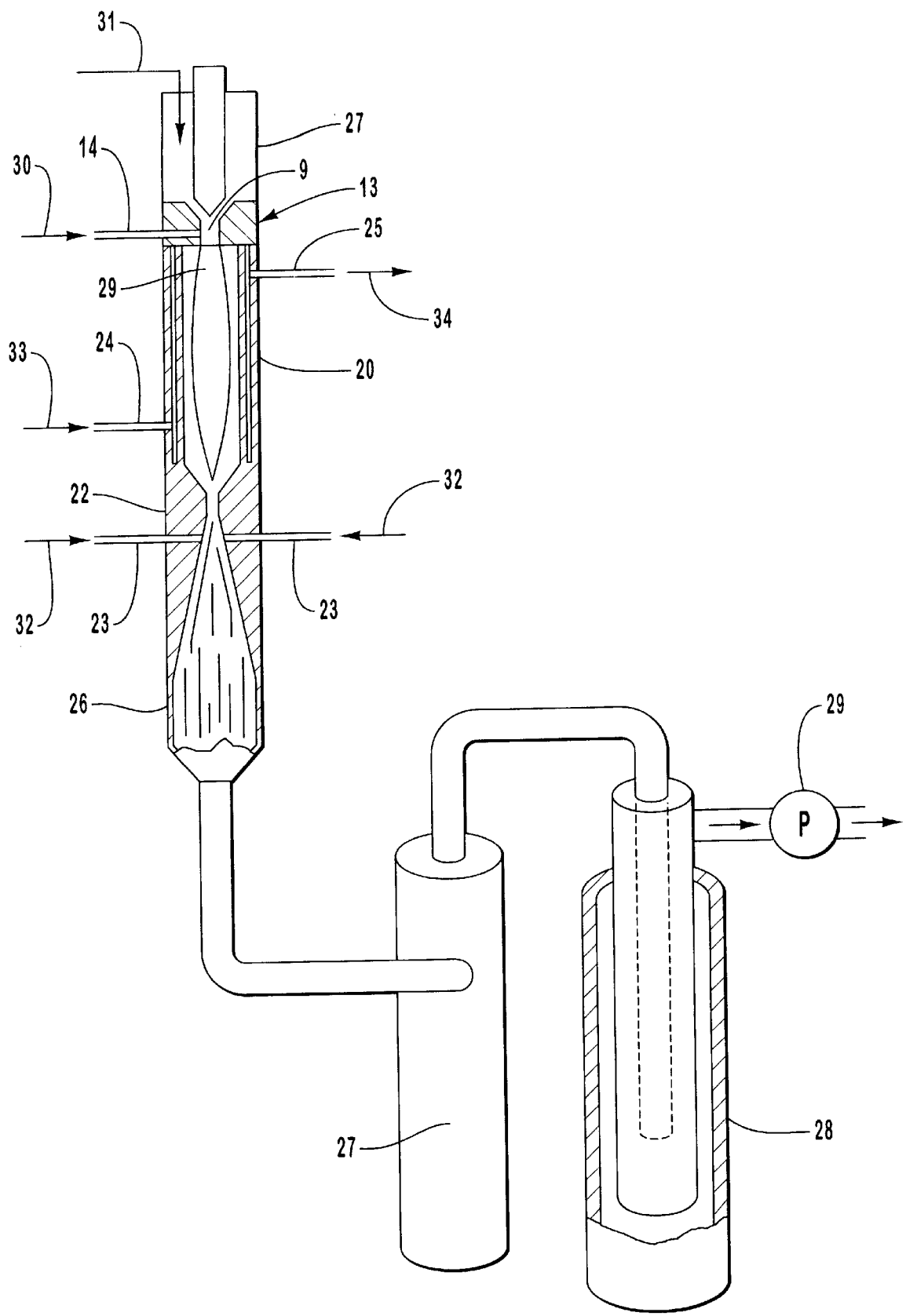
FIG. 1 is a schematic cross-sectional view of a reactor system.

A schematic diagram of a quenching apparatus is shown in FIG. 1. An enclosed axial reactor chamber 20 includes an inlet at one end (shown to the left) and an outlet at its remaining end (shown to the right).

A plasma device such as a plasma torch 21 is positioned adjacent to the reaction chamber. A plasma torch is preferred where the temperature of the plasma is preferably is elevated significantly above room temperature in order to accomplish the mixing and reacting of the reactant stream.

A plasma torch 21 is positioned adjacent to the reactor chamber. Torch 21 is used to thermally decompose an incoming gaseous stream within a resulting plasma 29 as the gaseous stream is delivered through the inlet of the reactor chamber 20.

A plasma is a high temperature luminous gas which is at least partially (1 to 100%) ionized. A plasma is made up of gas atoms, gas ions, and electrons. In the bulk phase a plasma is electrically neutral. A thermal plasma can be created by passing a gas through an electric arc. The electric arc will rapidly heat the gas by resistive and radiative heating to very high temperatures within microseconds of passing through the arc. The plasma is typically luminous at temperatures above 9000 K.

A plasma can be produced with any gas in this manner. This gives excellent control over chemical reactions in the plasma as the gas might be neutral (argon, helium, neon), reductive (hydrogen, methane, ammonia, carbon monoxide) or oxidative (oxygen, nitrogen, carbon dioxide).

The details of plasma generating torches are well known and need not be further detailed within this disclosure to make the present invention understandable to those skilled in this field.

An incoming stream of plasma gas is denoted by arrow 31. The plasma gas can also be a reactant or can be inert. Preferably, the plasma gas is hydrogen. A gaseous stream of one or more reactants (arrow 30) is normally injected separately into the plasma 29, which is directed toward the downstream outlet of the reactor chamber 20. The gaseous stream moving axially through the reactor chamber 20 includes the reactants injected into the plasma arc or within a carrier gas.

Reactant materials are usually injected downstream of the location where the arc attaches to the annular anode of the plasma generator or torch. Materials which can be injected into the arc region include natural gas, such as is used in the Huels process for the production of ethylene and acetylene from natural gas.

Gases and liquids are the preferred forms of injected reactants. Solids may be injected, but usually vaporize too slowly for chemical reactions to occur in the rapidly flowing plasma gas before the gas cools. If solids are used as reactants, they will usually be heated to a gaseous or liquid state before injection into the plasma.

A convergent-divergent nozzle 22 is coaxially positioned within the outlet of the reactor chamber 20. The converging or upstream section of the nozzle restricts gas passage and controls the residence time of the hot gaseous stream within the reactor chamber 20, allowing its contents to reach thermodynamic equilibrium. The contraction that occurs in the cross sectional size of the gaseous stream as it passes through the converging portions of nozzle 22 change the motion of the gas molecules from random directions, including rotational and vibrational motions, to straight line motion parallel to the reactor chamber axis. The dimensions of the reactor chamber 20 and the incoming gaseous flow rates are selected to achieve sonic velocity within the restricted nozzle throat.

As the confined stream of gas enters the diverging or downstream portions of nozzle 22, it is subjected to an ultra fast decrease in pressure as a result of a gradual increase in volume along the conical walls of the nozzle exit. The resulting pressure change rapidly lowers the temperature of the gaseous stream to a new equilibrium condition.

An additional reactant, such as hydrogen at ambient temperatures, can be tangentially injected into the diverging section of nozzle 22 (arrow 32) to complete the reactions or prevent back reactions as the gases are cooled. Supply inlets for the additional reactant gas are shown in FIG. 1 at 23.

Numerals 24 and 25 designate a coolant inlet and outlet for the double-walled structure of the reactor chamber 20. Coolant flow is indicated by arrows 33 and 34. The walls of nozzle 22 and a coaxial cool down chamber 26 downstream from it may also be physically cooled to minimize reactions along their inner wall surfaces.

Reaction product particles are collectable within a cyclone separator shown generally at 27. A downstream liquid trap 28, such as a liquid nitrogen trap, can be used to condense and collect reactor products within the gaseous stream prior to the gaseous stream entering a vacuum pump 29.

Figure 2:
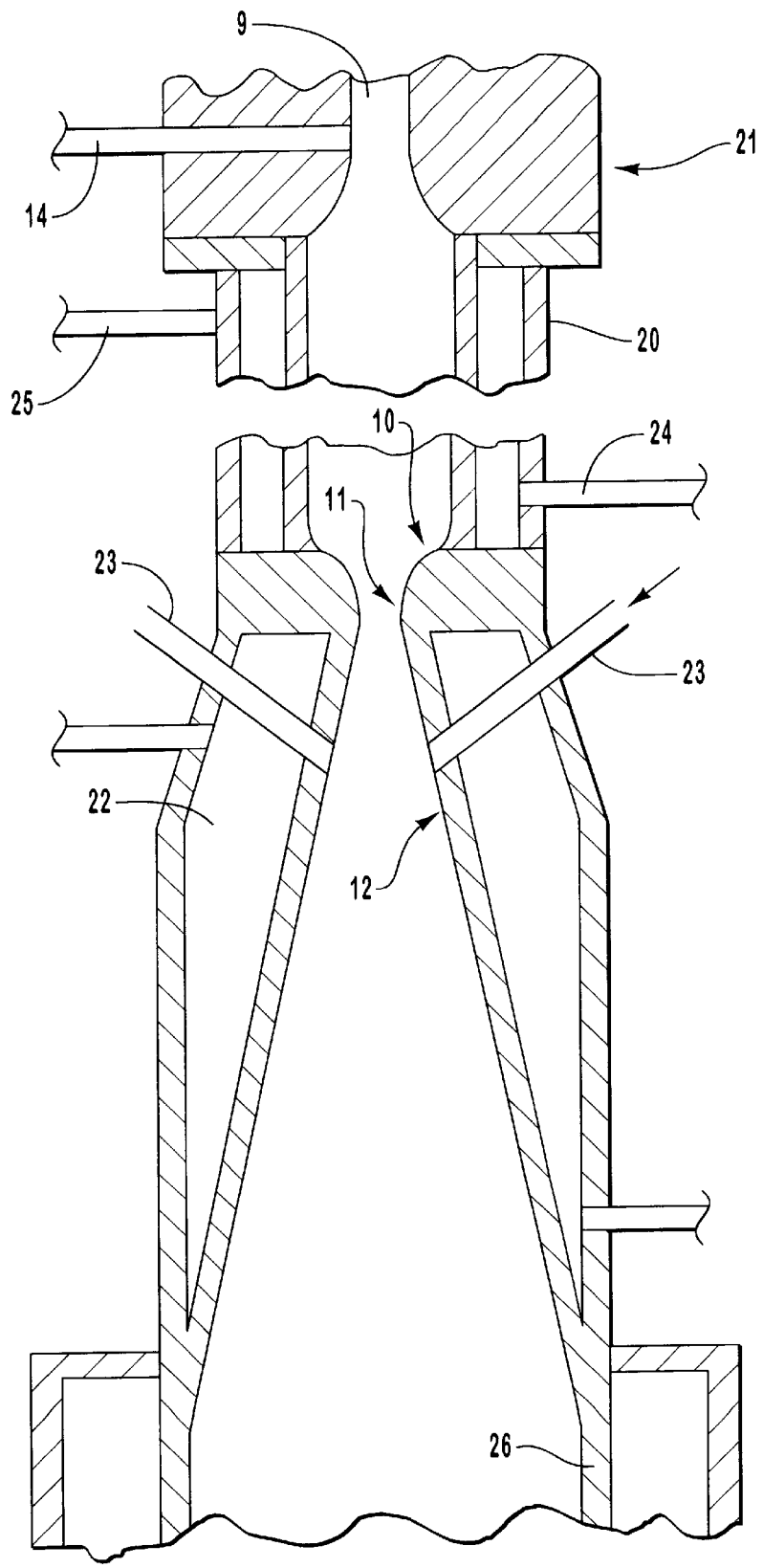
FIG. 2 is an enlarged cross-sectional view of the reactor chamber and converging-diverging nozzle.

FIG. 2 further illustrates details of the converging-diverging nozzle structure 22. The same reference numerals are used in FIG. 2 as in FIG. 1. By proper selection of nozzle dimensions, reactor chamber 20 can be operated at atmospheric pressure or in a pressurized condition, while cool down chamber 26 downstream from nozzle 22 is maintained at a vacuum pressure by operation of pump 29. The sudden pressure change that occurs as the gaseous stream traverses nozzle 22 brings the gaseous stream to a lower equilibrium condition instantly and prevents unwanted back reactions that would occur under more drawn out cooling conditions.

Typical residence times for materials within the free flowing plasma are on the order of milliseconds. To maximize mixing with the plasma gas the reactants (liquid or gas) are injected under pressure (10 to 100 atmospheres) through a small orifice at feed stream inlet 14 to achieve sufficient velocity to penetrate and mix with the plasma. It is preferable to use gaseous or vaporized reactants whenever practical, since this eliminates need for a phase change within the plasma and improves the kinetics of the reactor. In addition, the injected stream of reactants is injected about normal (about a 90° angle) to the flow of the plasma gases. In some cases positive or negative deviations from this 90° angle by as much as 30° may be optimum.

The high temperature of plasma 29 rapidly vaporizes the injected feed stream entering at inlet 14 and breaks apart gaseous molecular species to their atomic constituents. A variety of products are produced, principally carbon monoxide and diatomic hydrogen with minor amounts of acetylene, acetylene black, and elemental carbon among others. The products can be synthesized by injecting reactants in liquid or gaseous form into a plasma of the appropriate gas downstream from the anode arc attachment point and within the torch exit or along the length of the reactor chamber. Carbon monoxide and diatomic hydrogen are especially preferred products made according to this invention.

Reaction chamber 20 is the location in which the preferred chemical reactions occur. It begins downstream from the plasma arc inlet 9 and terminates at an outlet end 10 of reactor chamber 20. Outlet end 10 leads to the nozzle throat. It includes the reactor areas in which reactant injection/mixing and product formation occurs, as well as the converging section of the quench nozzle.

Temperature requirements within reactor chamber 20 and its dimensional geometry are specific to the temperature required to achieve an equilibrium state with an enriched quantity of each desired end product.

There is a substantial difference in temperature gradients and gaseous flow patterns along the length of the reactor chamber 20. At the plasma arc inlet 9, flow is turbulent and there is a high temperature gradient; from temperatures of about 20,000 K at the axis of the chamber to about 375 K at the chamber walls. At nozzle throat 11, the gaseous flow is laminar, the bulk temperature is in a range from about 500° C. to about 4,000° C., and there is a very low temperature gradient across its restricted open area.

Since reaction chamber 20 is an area of intense heat and chemical activity it is necessary to construct reactor chamber 20 of materials that are compatible with the temperature and chemical activity to minimize chemical corrosion from the reactants, and to minimize melting degradation and ablation from the resulting intense plasma radiation. Reactor chamber 20 may be constructed of water cooled stainless steel, nickel, titanium, or other suitable materials. Reactor chamber 20 can also be constructed of ceramic materials to withstand the vigorous chemical and thermal environment.

The walls of reactor chamber 20 are internally heated by a combination of radiation, convection and conduction. Cooling of the reactor chamber walls prevents unwanted melting and/or corrosion at their surfaces. The system used to control such cooling should maintain the walls at as high a temperature as can be permitted by the selected wall material, which must be inert to the reactants within the reactor chamber at the expected wall temperatures. This is true also with regard to the nozzle walls, which are subjected to heat only by convection and conduction.

The dimensions of the reactor chamber 20 are chosen to minimize recirculation of the plasma and reactant gases and to maintain sufficient heat (enthalpy) going into the nozzle throat to prevent degradation (undesirable back or side reaction chemistry).

The length of the reactor chamber 20 may be determined experimentally by first using an elongated tube within which the user can locate the target reaction threshold temperature. Reactor chamber 20 can then be designed long enough so that reactants have sufficient residence time at the high reaction temperature to reach an equilibrium state and complete the formation of the desired end products. Such reaction temperatures can range from a minimum of about 1500° C. to about 4000° C.

The inside diameter of the reactor chamber 20 is determined by the fluid properties of the plasma and moving gaseous stream. It must be sufficiently great to permit necessary gaseous flow, but not so large that undesirable recirculating eddies or stagnant zones are formed along the walls of the chamber. Such detrimental flow patterns will cool the gases prematurely and precipitate unwanted products, such as subchlorides or carbon. As a general rule, the inside diameter of the reactor chamber 20 should be in the range of 100 to 150 percent of the plasma diameter at the inlet end of the reactor chamber.

The purpose of the converging section of nozzle 22 is to compress the hot gases rapidly into a restrictive nozzle throat 11 with a minimum of heat loss to the walls while maintaining laminar flow and a minimum of turbulence. This requires a high aspect ratio change in diameter that maintains smooth transitions to a first steep angle (>45°) and then to lesser angles (<45°) leading into nozzle throat 11.

The purpose of nozzle throat 11 is to compress the gases and achieve sonic velocities in the flowing hot gaseous stream. This converts the random energy content of the hot gases to translational energy (velocity) in the axial direction of gas flow. This effectively lowers the kinetic temperature of the gases and almost instantaneously limits further chemical reactions. The velocities achieved in nozzle throat 11 and in the downstream diverging section of nozzle 22 are controlled by the pressure differential between the reactor chamber 20 and the section downstream of the diverging section of nozzle 22. Negative pressure can be applied downstream or positive pressure applied upstream for this purpose, referred to as cool down chamber 26.

The purpose of the diverging section of nozzle 22 is to smoothly accelerate and expand gases exiting nozzle 22 from sonic to supersonic velocities, which further lowers the kinetic temperature of the gases.

The term "smooth acceleration" in practice requires use of a small diverging angle of less than 35 degrees to expand the gases without suffering deleterious effects of separation from the converging wall and inducing turbulence. Separation of the expanding gases from the diverging wall causes recirculation of some portion of the gases between the wall and the gas jet exiting nozzle throat 11. This recirculation in turn results in local reheating of the expanding gases and undesirable degradation reactions, producing lower yields of desired end products.

Physics of the Nozzle

The fast quench phenomena observed in this reactor is achieved by rapidly converting thermal energy in the gases to kinetic energy via a modified adiabatic and isentropic expansion through converging-diverging nozzle 22. In the process, the gas temperature and pressure drop extremely fast and the gas reaches supersonic velocity. It is preferable to first raise the temperature of the reactants in the reactor chamber to a level at which the desired end product is more stable than other reaction products in equilibrium with it. This is normally a consequence of the fact that the free energy of the desired end product will decrease at the selected elevated temperatures in comparison to the remaining reaction products. However, this window of opportunity is very short-lived about ($<10^{-3}$ sec or shorter) in a high temperature reactor. To stabilize maximum conversion of the reaction product, it is necessary to rapidly cool the emerging gas below a selected cooling temperature to force it to a lower equilibrium state and thereby prevent decomposition of the end product.

To understand the quench phenomenon in this reactor, it is necessary to investigate the changes in the temperature, pressure, and velocity of the gases as a function of changes in reactor geometry.

Reactor nozzle 22 (FIG. 2) can be divided into three sections; the convergent reaction chamber 10, the nozzle throat 11, and the divergent quench chamber 12. The entrance angle to the throat area, the cross-sectional area of the throat, and the diverging angle after the throat all exert influence on the temperature, pressure, and velocity profiles of the plasma gas.

In converging-diverging nozzle 22, the gas is flowing from a higher pressure $P_0$ to a lower pressure $P_1$. During passage of the gas through nozzle 22, there will be a rapid transformation of thermal energy to kinetic energy. This kinetic energy will give rise to a high gas velocity after discharging from nozzle 22. The gas enters the converging section at a low velocity and will emerge at the diverging section with a higher velocity.

The velocity of the gas in the throat of the nozzle, assuming adiabatic expansion, will achieve sonic values. When the gas accelerates through the nozzle throat, the temperature of the gas will, simultaneously drop rapidly. As a result of high velocity cooling, the initial gas temperature ($T_0$) will drop to a lower temperature, $T_1$, upon exiting from the nozzle. This rapid temperature quenching through a nozzle freezes the high temperature equilibrium products of a high temperature gas phase reaction. The pressure and temperature drop resulting from adiabatic expansion in a converging-diverging nozzle is described in the following equation:

$$\left(\frac{P_0}{P_1}\right)^{\frac{\gamma-1}{\gamma}} = \frac{T_0}{T_1}$$

$P_0$, $P_1$, $T_0$ are initial and final pressures and temperatures of the gas, respectively. $\gamma$ is the ratio of $C_p/C_v$ where $C_p$ and $C_v$ are the heat capacities at constant pressure and volume, respectively. At 2500 K, $\gamma$ is 1.66 for Ar, 1.30 for $H_2$, and 1.11 for $C_2H_2$. This equation can be used to estimate the temperature drop across the nozzle throat if the initial and final pressures of the gases are known or vice versa. The mass flow rate, m, is related to the cross-sectional area (A*) of the nozzle throat, the velocity (V) and the specific volume ($\Omega$) of the gas at the throat. The specific volume ($\Omega$) is the inverse of gas density at the cross section.

$$\dot{m} = \left(\frac{V}{\Omega}\right) \times A^*$$

After substituting $T_0$, $P_0$, $\gamma$, M (molecular weight), and R (the gas constant) for $V/\Omega$, the equation takes the form:

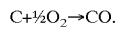

This equation has been used to guide the design of the nozzle diameters used in the reactors built to date. Despite the assumption for constant γ (which is valid for an argon plasma), the equation has been quite accurate in predictions of mass flow as a function of temperature, pressure, molecular weight, and nozzle diameter compared to experimental results.

The velocity of the expanding gas in mach number (Ma) is related to temperature (T), pressure (P), density ($\rho=\Omega^{-1}$), and nozzle area (A) by the following equations:

$$\frac{T_0}{T} = 1 + \frac{\gamma-1}{2}(Ma)^2$$

$$\frac{P_0}{P} = \left[1 + \frac{\gamma-1}{2}(Ma)^2\right]^{\gamma/(\gamma-1)}$$

$$\frac{\rho_0}{\rho} = \left[1 + \frac{\gamma-1}{2}(Ma)^2\right]^{\gamma/(\gamma-1)}$$

$$\frac{A}{A^*} = \frac{1}{Ma}\left\{\frac{2}{\gamma+1}\left[1 + \frac{\gamma-1}{2}(Ma)^2\right]\right\}^{(\gamma+1)/[2(\gamma-1)]}$$

In the last equation above, A* is the cross-sectional area at the throat of the nozzle, and A is the cross-sectional area of the converging-diverging section. Substituting $T_0/T$ into the equation, it becomes:

$$\frac{A}{A^*} = \frac{1}{Ma}\left\{\frac{2}{\gamma+1} \times \frac{T_0}{T}\right\}^{(\gamma+1)/[2(\gamma-1)]}$$

Figure 3:
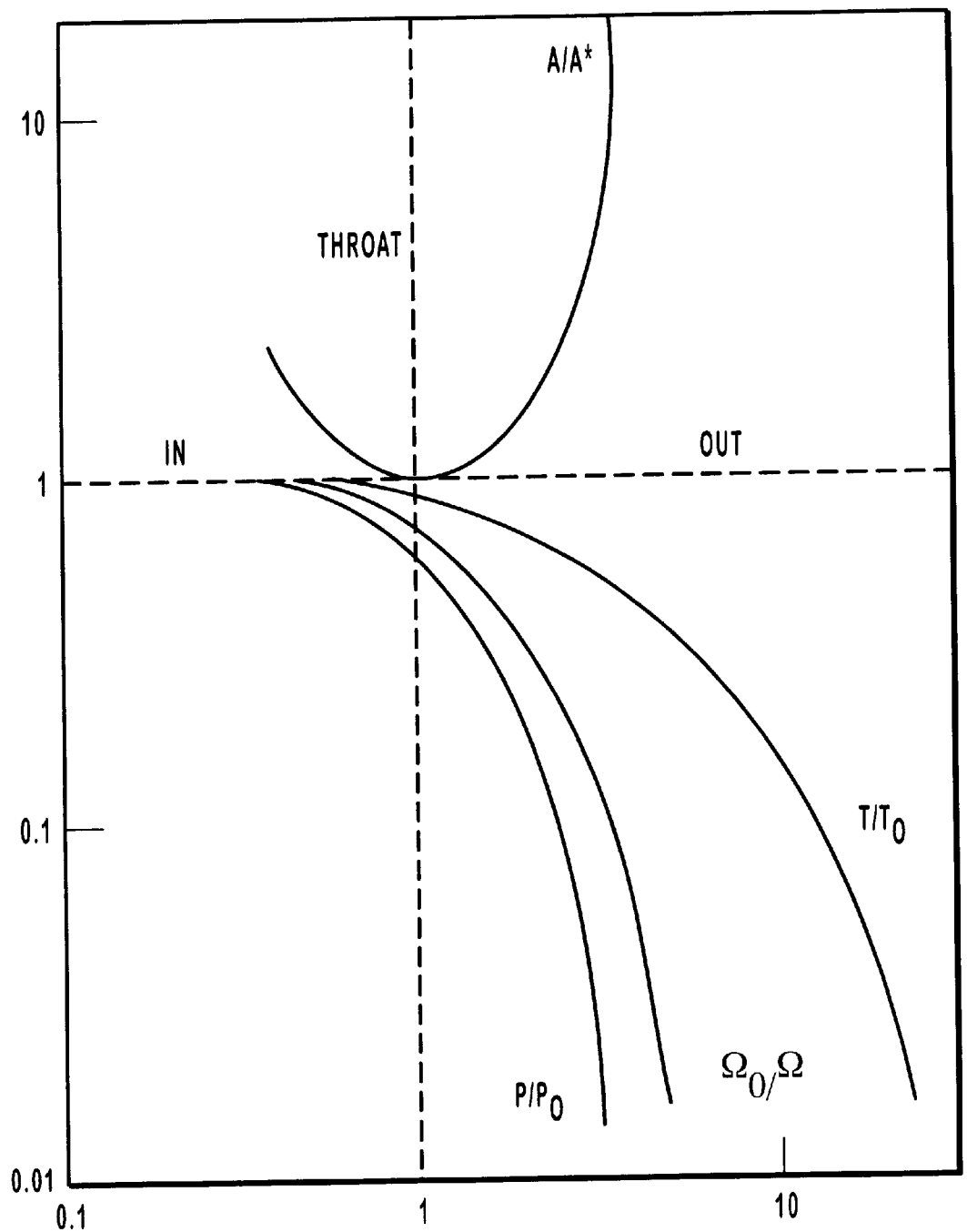
FIG. 3 is a plot of temperatures, pressures, specific volumes and nozzle throat areas as a function of gas velocity in the reactor apparatus.

FIG. 3 is a plot of $T/T_0$, $P/P_0$, $\Omega_0/\Omega$, and $A/A^*$ through a nozzle throat as a function of the gas velocity (in Ma) for γ=1.3 ($H_2$). It clearly demonstrates that both gas temperature and pressure quench rapidly upon exiting from the nozzle. The resulting high gas velocity lends itself to the application of a gas-turbine to recover some of the energy as electricity to supplement the process.

In a test case (using a 95% Ar and 5% $H_2$ plasma) if A/A*=4, Ma=2, and γ=1.66 the final temperature drops almost by a factor of 4. This type of temperature drop is easily attainable through the quench nozzle. If the final temperature in the quench chamber for a reaction is 500 K, then the initial temperature before the quench nozzle would be around 1,500 K.

The present invention is related to a method of thermally converting one or more carbon-containing reactants in a high temperature gaseous stream to at least one reaction product, preferably carbon monoxide. The present invention also may use a source of oxygen atoms in order to produce the carbon monoxide product. Reactants, as a source of carbon atoms and a source of oxygen atoms, may be such light hydrocarbons as methane, ethane, propane, butane, and the like. As such, light hydrocarbons and the like require a source of oxygen atom in order to make carbon monoxide.

Another source of carbon atoms is pure carbon such as carbon black and the like. In its simplest form, production of carbon monoxide may be carried out using pure carbon and carbon dioxide according to the following equation:

$C+CO_2 \rightarrow 2CO$.

Alternatively, pure carbon and oxygen may be used to form carbon monoxide according to the following equation:

$C+\frac{1}{2}O_2 \rightarrow CO$.

EXAMPLE

Carbon Monoxide from Carbon Dioxide

The preferred method for producing carbon monoxide from carbon dioxide involves directing carbon dioxide gas into a hot plasma torch operated at about 12 kW with a mixture of argon and hydrogen as the plasma gas (95% Argon: 5% Hydrogen, by volume) to decompose it to carbon monoxide and oxygen, followed by rapid expansion of the resulting hot gases and cooling with additional gases to retain the carbon monoxide in a substantially pure and stable room temperature state.

Figure 4:
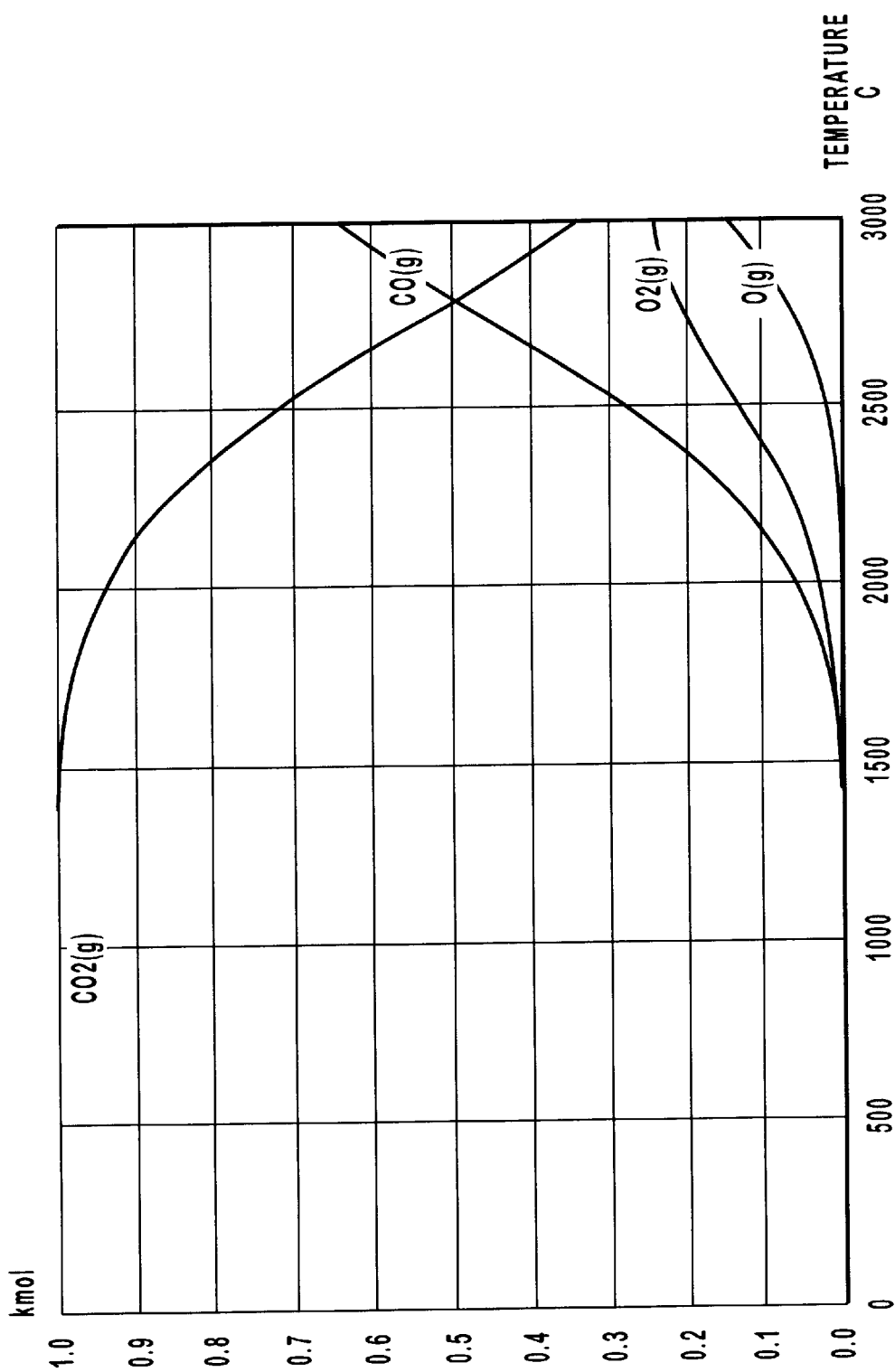
FIG. 4 is a graph plotting equilibrium concentrations in a carbon dioxide system as a function of temperature.

FIG. 4 is an equilibrium diagram that shows carbon dioxide and decomposition products as a function of temperature. In FIG. 4, carbon dioxide begins to decompose at about 1,500° C. and higher. At about 2,800° C., the carbon dioxide is about half decomposed into carbon monoxide, diatomic oxygen, and monatomic oxygen. In the system at about 2,800° C., there remains about half of the carbon dioxide that was present before heating. The length of the reactor is chosen, in connection with temperature requirement, such that the preferred equilibrium state of the system exists at the nozzle throat.

The diameter and length (6.0 mm×700.0 mm) of the reaction chamber is chosen to obtain maximum mixing of plasma gas and reactant gas while maintaining a minimum of 3,000 K temperature at the entrance of the nozzle throat. The reactor chamber, converging/diverging nozzle were constructed from nickel 200 alloy to reduce corrosion. Standard equations were used to calculate the dimensions of the bell-shaped converging nozzle, nozzle throat diameter diverging angle, and diverging nozzle exit diameter.

Reactants: Carbon dioxide

Plasma Torch: 10 kW laboratory plasma torch
   30 Volts, 400 Amps
   Cathode: thoriated tungsten in water cooled copper
   Anode: Water-Cooled Copper Cylinder 6.0 mm diameter×20.0 mm in length Plasma Gas: 95% Argon, 5% Hydrogen, Average total gas flow was maintained at 23.6 liters/min.

Reactant Injection: Gaseous (200° C.) carbon dioxide at the point where the plasma plume exits the plasma torch. The hot carbon dioxide injection tubes, reaction chamber and converging/diverging nozzle section were constructed from nickel 200 alloy to minimize corrosion.

Injection Rate: Gaseous carbon dioxide was injected at the rate of 10.0 to 15.0 milliliters/hour. This resulted in a carbon monoxide gas production rate of 6.3 grams per hour.

Reaction Chamber: Water-cooled Nickel 200 cylinder 6.0 mm×20.0 mm

Converging Nozzle: Bell shaped with 2.0 mm radii

Nozzle throat: 2.0 mm×1.0 mm in length, determined from standard equations,

Diverging Nozzle: Conical shaped with 14° included angle expanding out to a 12.0 mm diameter.

Cool down section: Water-cooled stainless steel, 12.0 mm diameter×600.0 mm

Cyclone collectors: Water-cooled stainless steel, 12.0 mm inlet and outlet diameter, 50.0 mm inside diameter body, designed to maintain high entrance and exit velocity Off-Gas Cleanup: After product collection the process gas was passed through a liquid nitrogen cold trap and HEPA filter to remove impurities before the gas entered the mechanical vacuum pump.

Vacuum System: A mechanical vacuum pump was used to maintain pressure downstream from the nozzle throat at 5.0 to 10.0 Torr (mm Hg)

FIGS. 1 and 2 of the drawings pertain to an apparatus tested for converting carbon dioxide. In the described preferred embodiment, the preferred product is carbon monoxide and the reactant is carbon dioxide. However, the illustrated apparatus is suitable for use with other compositions and compounds where plasma processing of the compound requires ultra fast quenching to prevent back reactions.

The plasma torch 21 located at the reactor chamber inlet thermally decomposes an incoming gaseous stream comprised of a carbon dioxide-containing mixture plus one or more reactants as the resulting gaseous stream moves axially through reactor chamber 20 in conjunction with a carrier gas. The resulting hot gaseous stream is then directed through the coaxial convergent-divergent nozzle 22. The convergent portion 10 of the nozzle 22 controls the residence time of the hot gaseous stream within reactor chamber 20, thereby allowing its contents to reach thermodynamic equilibrium. It also streamlines the flow of hot gases, converting their motion from random movement to straight line movement along the central nozzle axis. The divergent portion 12 of nozzle 22 subjects the stream to an ultra fast decrease in pressure. Quenching streams of gas, normally at ambient temperature, may be introduced into the hot gaseous stream through inlets 23 as it passes through the nozzle. This rapidly cools the contents of the hot gaseous stream at a rate that condenses the carbon monoxide and inhibits formation of unwanted products.

The plasma reduction is based on a quasi equilibrium-temperature quench sequence in which the initiation of nucleation is controlled by passage of a heated gaseous stream through a converging-diverging nozzle geometry.

Conditions necessary for complete dissociation of carbon dioxide in a hydrocarbon stream into carbon monoxide can be predicted using free energy minimization techniques which assume thermodynamic equilibrium.

Figure 5:
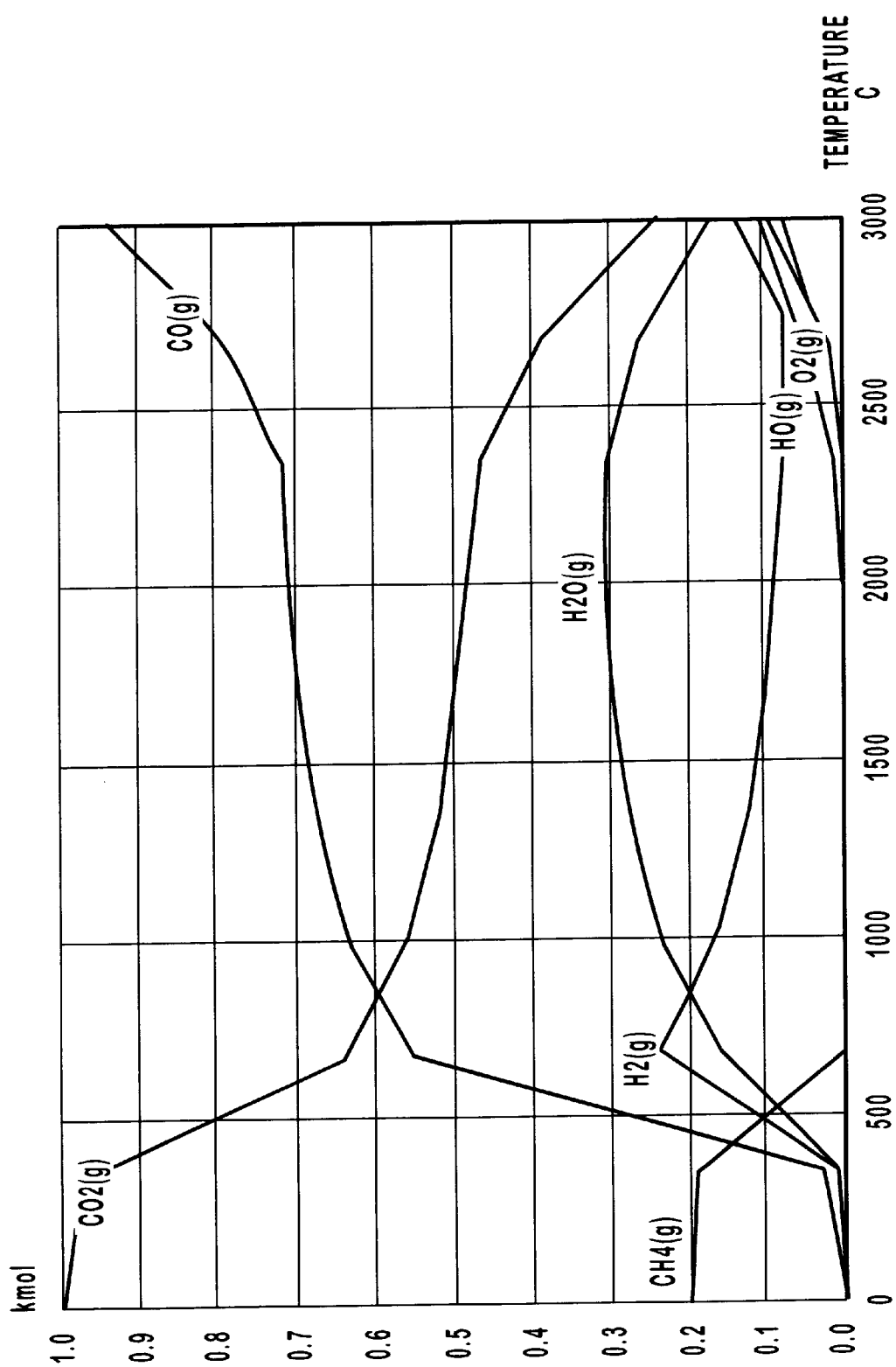
FIG. 5 is a graph plotting equilibrium concentrations in a carbon dioxide and methane system as a function of temperature, with a methane-to-carbon dioxide ratio of 0.2:1.

FIG. 5 shows the carbon dioxide and methane species as a function of temperature for a system at 1 atm. When argon is taken into account (to 96%) there is basically no change in the relative species distribution. As seen in FIG. 5, as carbon dioxide is heated in the presence of methane at a ratio of 0.2 parts methane to 1 part carbon dioxide, decomposition reaches 40 percent carbon dioxide decomposed and methane substantially decomposed near about 800° C. Where it is desirable to minimize carbon dioxide and to also minimize water production, the reactor is lengthened sufficient to cause the system to heat to about 3,000° C. or higher. The water is easily removed from the product stream by condensation. Where it is desirable to minimize the occurrence of the HO and O2 species, the reactor length is configured to freeze the system once it reaches about 2,000° C. At this temperature, the presence of H2 and carbon dioxide are significant.

In a rapidly cooling plasma system one can think of the gas in equilibrium at temperature $T_0$ and pressure $P_0$ being suddenly quenched in temperature and pressure. For $CO_2$ about at 3000 K, a chemical equilibration time of less than 10 nsec is possible. At this temperature the reactants should be well equilibrated. As the plasma cools this characteristic time increases until at a particular T and P, the cooling rate becomes greater than the equilibrium rate and the composition of the plasma is "frozen." On further temperature decrease, the vapor pressure of one component subsystem becomes greater than the saturation vapor pressure and nucleation occurs. When this subsystem is charged, condensation is enhanced for that species.

Taking into consideration the free energy equilibrium condition shown in FIG. 5, in order to avoid more that 0.5 mole fraction carbon dioxide in the product stream, the gas must be frozen at temperatures above 3,100 K. Freezing the mixture at even lower temperatures will result in a substantial amount of carbon dioxide vapors. It is clear from this that a higher temperature quench will result in a better yield of the desired carbon monoxide end product.

Experimental conditions for selective formation of carbon monoxide plasma depend on specific values of rate coefficients and upon the initial temperature and pressure $T_0$ and $P_0$ at which the plasma is frozen. The carbon monoxide product is also dependent on the cooling rate of the plasma and upon the geometry of the reactor. Of course not all reaction pathways become "frozen" at the same temperature during quench.

The converging-diverging nozzle configuration used in supersonic flow applications offers possibilities to control both the temperature quench rate and the concentration at which the plasma becomes "frozen" during the expansion. The converging-diverging DeLaval nozzle and the associated Prandtl-Meyer expansion process are discussed in standard texts on compressible fluid flow. In such expansion nozzles the hot plasma gas undergoes an approximate isentropic expansion and the energy in the gas (its enthalpy) is converted to unidirectional velocity in the diverging nozzle. When the exit pressure is sufficiently low, it is possible to reach supersonic speeds. Non-adiabatic expansion processes which are attained in practice aid in the resultant temperature search.

A number of experiments with carbon dioxide and methane gas injected into an argon or argon-hydrogen plasma are provided. The dimensions and geometry of the reactors are varied. Provisions are made for gas quenching at the throat exit.

Methane and carbon dioxide conversion to hydrogen and carbon monoxide in a high temperature reactor follow the theoretical chemical reaction: $CO_2+CH_4 \rightarrow 2CO+2H_2$. In principle, under careful kinetic studies on the pyrolysis of methane it has been shown that it is possible to obtain high yields of acetylene where the main by-product is hydrogen, instead of tars and acetylene black. Such studies also showed that pyrolysis in the presence of hydrogen suppressed carbon formation.

In practice, a range of other hydrocarbons, specifically the light olefins and solid carbon, may be formed as byproducts including acetylene if the reaction condition is not well controlled.

Experiments using the fast quench system of this disclosure revealed that the methane decomposition to acetylene is kinetics controlled rather than equilibrium controlled. These results point to the advantage of high quench rates which provide opportunities to preserve high temperature equilibrium products.

FIGS. 6–9 show the equilibrium compositions of methane conversion to hydrogen and carbon dioxide decomposition to carbon monoxide. It is seen from these figures that the amount of methane has a directly proportional effect on both hydrogen and carbon monoxide production amounts.

Other Examples

The inventive method for thermally converting one or more carbon-containing reactants in a thermodynamically stable high temperature gaseous stream to at least one reaction product, comprises the following steps. Carbon dioxide containing the reactant stream is introduced at one axial end of a reaction chamber containing an ionized gas. The carbon dioxide containing reactant stream is heated in the reaction chamber to form a carbon monoxide containing reaction product stream. The reaction chamber has a predetermined length sufficient to effect heating of the carbon dioxide containing reactant stream to a temperature at which carbon monoxide is available as a reaction product stream at a location adjacent the outlet end of the reaction chamber. The reaction product is expanded through the outlet end of the reaction chamber to cool the gaseous stream by converting thermal energy to kinetic energy as the reaction product expands. The reaction product is then cooled to room temperature. The ionized gas is preferably hydrogen.

An initial experiment to produce carbon monoxide and hydrogen is conducted using the plasma fast quench process. A nontransferred plasma torch is operated at 3 kW input power.

The reaction chamber, converging/diverging nozzle and downstream cool down chamber were constructed of copper coated with an alumina type ceramic. The purpose of the ceramic was to prevent corrosion of the copper by reaction product gases in this process and reduce heat loss from the reaction zone.

The reactor chamber for this original system test was 2.0 cm in diameter by 10.0 cm in length. The quench section including the cool down chamber consisted of a 90° included angle converging section followed by a 3.0 mm diameter throat and a 90° included angle diverging section issuing into a 4.0 cm diameter by 20 cm long cool down chamber. Four tangential hydrogen gas jets (1.0 mm diam) were placed in the diverging section of the nozzle approximately 5 mm downstream from the nozzle throat. Quenching could also be accomplished by reducing the expansion angle of the diverging section of the nozzle to less than a 20° included angle, with the optimum diverging included angle being 6° to 14°.

As a further example of dimensional design for a laboratory-scale reactor, subsequent tests were conducted using a reactor chamber length of 20 mm, although tests have been conducted with reactor chamber lengths ranging to 150 mm lengths. The plasma inlet opening was 6 mm and the reactor chamber interior diameter was 11 mm. The downstream cool down section after the nozzle was typically 1 to 1.3 m, although lengths ranging from 0.3 to 4 m have been tested. The cool down section can be constructed as long as required to reach a desired final temperature in the exiting gaseous stream and products contained within it.

The system used for proof of concept experiments was based on approximations of anticipated velocity, pressure, and temperature profiles. While formation of carbon black is of concern because it reduces yield, this can be minimized by experimentally determining the optimum location of quenching. Similarly, the choice of materials of construction for this equipment can be important, as certain materials catalyze undesirable reactions or conversely can catalyze the desirable reactions.

The quench reaction zone geometry was optimized by conducting two dimensional modeling of the fluid dynamics of such a system. Modeling results determined that reaction zone diameter should be no larger than 200% of the plasma torch anode exit diameter with the optimum being 110% to 150%. This prevents recirculation of reaction gases in the reaction zone which would contribute to undesirable side reactions and decrease product yields.

Gas temperatures were measured experimentally along an elongated reactor chamber and were also modeled using a two dimensional fluid dynamics model to determine the optimum length of the reaction zone before the converging section. A reaction zone length was chosen from this data for a given plasma input power level, plasma gas flow, and reactant input rate which would result in gas temperatures at the entrance to the nozzle throat to be equal to or preferably greater than the required equilibrium temperature of the desired end product.

A high aspect ratio converging section was designed such that the radius of the convex and concave surfaces leading into the nozzle throat were approximately equal to the diameter of the nozzle throat. This converging geometry allows achieving the highest possible velocity at the entrance to the nozzle throat while limiting heat loss to the walls of the converging section or separation of the gas flow from the converging surface.

The optimum area (diameter) of the nozzle throat was calculated from equations available in texts pertaining to nozzle design. The nozzle throat was designed so that with the temperature, gas composition, mass flow, and pressure of the gas entering the nozzle known (or estimated) sonic or near sonic gas velocities are achieved in the nozzle throat. To achieve maximum cooling (temperature drop) the nozzle throat should be as short as possible. This is demonstrated by two equations for two-dimensional nozzle flow, with $R^*$ and $h^*$ designating the radius of curvature and throat height respectively:

$$\left[ \frac{d\left(\frac{T}{T_0}\right)}{dt} \right]^* = -(R^* h^*)^{1/2} \frac{\gamma - 1}{\left(\frac{\gamma + 1}{2}\right)^2} a_0$$

$$\left[ \frac{d\left(\frac{T}{T_0}\right)}{dt} \right]^* = -C a_0 (R^* h^*)^{-1/2}$$

where $T_0$ and $a^0$ are the gas temperature and speed of sound respectively in the reaction zone. In the second equation above, all constants for a given gas are collected in C. for air (gamma=7/5 or 1.4, C=0.278). Examination of these equations shows that greater cooling rates occur for smaller nozzle diameters and shorter nozzle lengths with generally smaller $R^*$ and $h^*$.

The divergence angle and area at the exit of the diverging nozzle were determined from standard texts on fluid dynamics and aerospace rocket motor design. In addition, two dimensional models of fluid flow under expected experimental conditions were also used to optimize the divergence angle and exit area of the nozzle. It was concluded that the optimum divergence included angle was less than 35° and preferably in the range of 10° to 14° for optimum expansion and acceleration of the gas. The maximum exit area (diameter) of the diverging nozzle was again determined by calculation from equations available in standard texts on fluid flow and rocket engine design.

The maximum allowable nozzle exit area depends on the mass flow through the nozzle and pressure difference between the reaction zone and the downstream cooling section. Choice of too large an expansion angle or too large an exit area will result in the gas flow "peeling off" or separating from the wall, which results in the undesirable conditions of turbulence, gas recirculation, gas reheating, and side or back reaction degradation of the desired end products.

The purpose of the cool down section of the plasma fast quench reactor device is to reduce the gas velocity while removing heat energy (which results from the decrease in velocity) in the gas at a rate sufficient to prevent the gas from increasing in kinetic temperature. Passage of the gaseous stream through the restrictive nozzle opening reduces its kinetic temperature, but remove no energy from the gas. The exiting gaseous stream is slowly warmed as some random motion of the gaseous contents is restored. This heat must be immediately removed from the system as it is produce, thereby maintaining the kinetic temperature of the resulting gaseous stream at a desired equilibrium level and preventing back reactions downstream from the nozzle.

Cool down or the reaction product gases has been accomplished by the use of length of water cooled tube having the same internal diameter as the internal exit diameter of the diverging section of the nozzle. With other applications of this device, it may be more desirable to supplement gas cooling by use of other types of heat exchangers.

Plasma quench processes for production of ultrafine materials require product collection capability downstream of the quench nozzle, preferably downstream of the cool down section. Bench scale experiments to date have used cyclonic collectors of standard dimensions described in the literature for gas and mass flows several time smaller than called for in the literature. This accommodates sonic or near sonic gas velocities through the cyclones, which allows efficient removal of ultrafine material (10 to 50 nm diameter powders).

In addition to mass flow and nozzle diameter, the third process parameter that determines the temperature drop across the nozzle is the ratio of the up stream pressure ($P_0$, in reaction zone) to the downstream pressure ($P_1$, cool down zone). In bench scale tests for the production of titanium metal powder and other materials, the ratio $P_0/P_1$ of 0.01 to 0.26 was maintained. The experimental systems were operated with the reaction zone pressure of approximately 700 to 800 Torr (ca. 1 atm.) and downstream pressure maintained between 10 and 200 Torr (0.26 to 0.01 atm.). In bench scale experiments, the low downstream pressure was accomplished using a mechanical vacuum pump.

In the following examples, the length and diameter of the reactor chamber are configured to maintain a temperature of about 1,500 C. at the entrance of the converging nozzle. The nozzle throat diameter is configured to achieve sonic velocity of the reaction product gas in the throat. Downstream from the nozzle throat, gas rapidly but gradually expands, geometrically speaking. The rapidly but gradually expanding gas acts to decompose any hydrocarbon gases such as acetylene, ethylene, and other low molecular weight hydrocarbons and others, that may have formed in the reaction chamber. The rapid but gradual expansion of the reaction product gas also fixes the chemical composition of the gas and prevents decomposition of the carbon monoxide back to carbon dioxide.

Any elemental carbon or other solids such as acetylene black is separated from the reaction products stream by use of a cyclones and the like or filters and the like or water and/or oil spray devices and the like.

The plasma gun is operated in a range from about 50 to about 100 kWhr input power at a potential in a range from about 100 to about 500 volts. Hydrogen plasma gas, as the preferred plasma gas, flows at a feed rate from about 300 to about 1,000 cubic foot per hour. Carbon dioxide, or carbon dioxide and methane are supplied to the reaction chamber at a rate from about 100 to about 1,500 cubic foot per hour.

In an embodiment of the present invention in which carbon dioxide is a substantially pure feed stock that makes up most of the feed stream, conversion is accomplished at about 2,500 C. FIG. 4 illustrates equilibrium conditions for this example. Under reactor chamber conditions of about 2,500 C at the nozzle entrance, the reaction product includes about 0.3 mole carbon monoxide, about 0.7 mole carbon dioxide, and the balance impurities.

In another general embodiment, the carbon dioxide containing reactant stream further comprises methane. In another embodiment, the carbon dioxide containing reactant stream further comprises methane in a methane to carbon dioxide ratio of about 0.2:1. FIG. 5 illustrates equilibrium conditions for this example. Under reactor chamber conditions of about 1,500 C at the nozzle entrance, the reaction product includes about 0.7 mole carbon monoxide, about 0.5 mole carbon dioxide, about 0.1 mole diatomic hydrogen, about 0.3 mole water, and the balance impurities.

Figure 6:
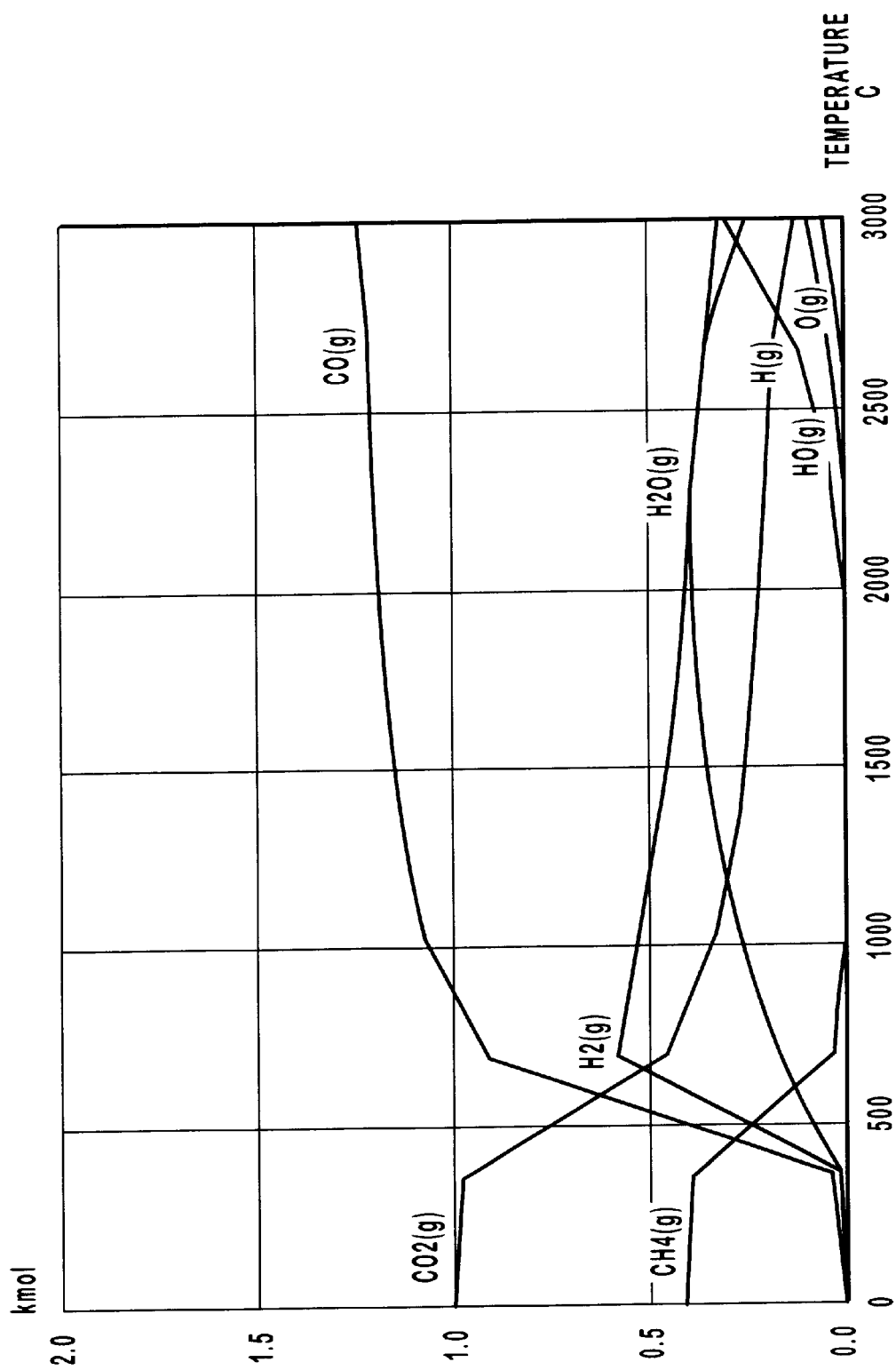
FIG. 6 is a graph plotting equilibrium concentrations in a carbon dioxide and methane system as a function of temperature, with a methane-to-carbon dioxide ratio of 0.4:1.

In another embodiment, the carbon dioxide containing reactant stream further comprises methane in a methane to carbon dioxide ratio of about 0.4:1. FIG. 6 illustrates equilibrium conditions for this example. Under reactor chamber conditions of about 1,500 C at the nozzle entrance, the reaction product includes about 1.2 mole carbon monoxide, about 0.25 mole carbon dioxide, about 0.5 mole diatomic hydrogen, about 0.4 mole water, and the balance impurities.

Figure 7:
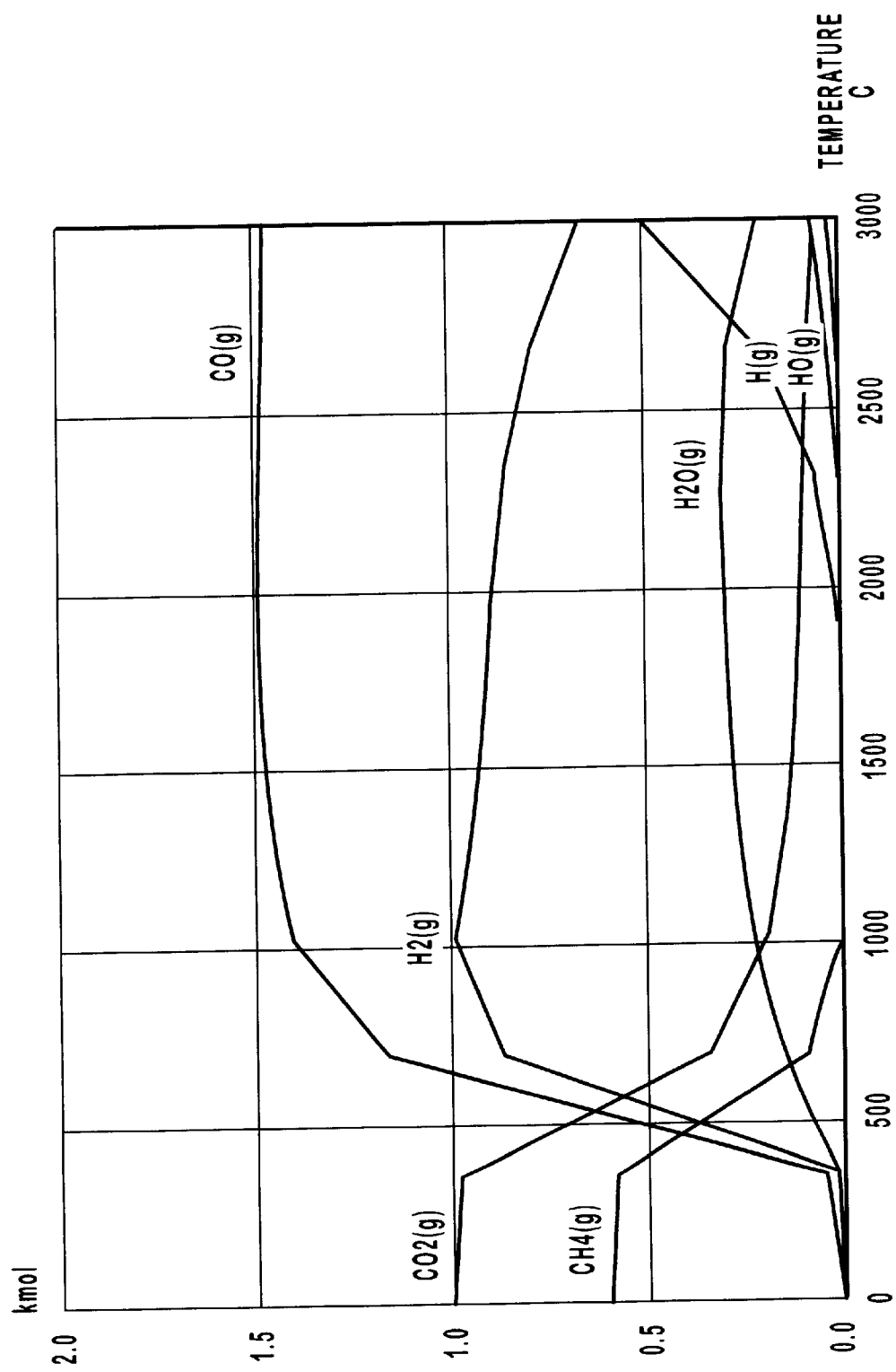
FIG. 7 is a graph plotting equilibrium concentrations in a carbon dioxide and methane system as a function of temperature, with a methane-to-carbon dioxide ratio of 0.6:1.

In another embodiment, the carbon dioxide containing reactant stream further comprises methane in a methane to carbon dioxide ratio of about 0.6:1. FIG. 7 illustrates equilibrium conditions for this example. Under reactor chamber conditions of about 1,500 C at the nozzle entrance, the reaction product includes about 1.5 mole carbon monoxide, about 0.2 mole carbon dioxide, about 0.9 mole diatomic hydrogen, about 0.25 mole water, and the balance impurities.

Figure 8:
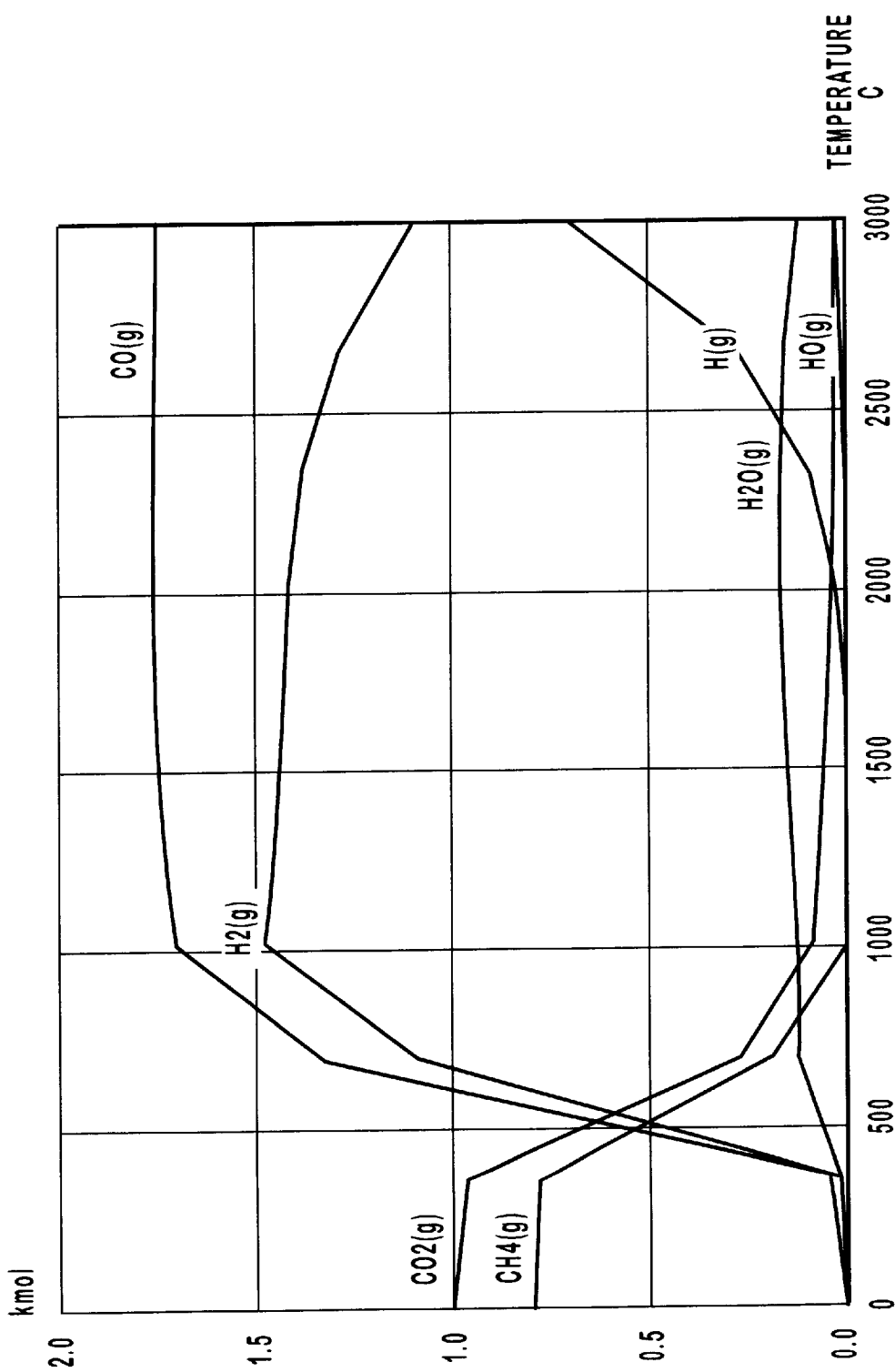
FIG. 8 is a graph plotting equilibrium concentrations in a carbon dioxide and methane system as a function of temperature, with a methane-to-carbon dioxide ratio of 0.8:1.

In another embodiment, the carbon dioxide containing reactant stream further comprises methane in a methane to carbon dioxide ratio of about 0.8:1. FIG. 8 illustrates equilibrium conditions for this example. Under reactor chamber conditions of about 1,500 C at the nozzle entrance, the reaction product includes about 1.75 mole carbon monoxide, about 0.1 mole carbon dioxide, about 1.5 mole diatomic hydrogen, about 0.2 mole water, and the balance impurities.

In the present invention, heating is preferably accomplished by introducing a stream of plasma arc gas to a plasma torch at the one axial end of the reactor chamber to produce a plasma within the reaction chamber which extends toward its remaining axial end. Additionally, cooling the reaction product is preferably accomplished by use of a restrictive convergent-divergent nozzle.

Figure 9A:
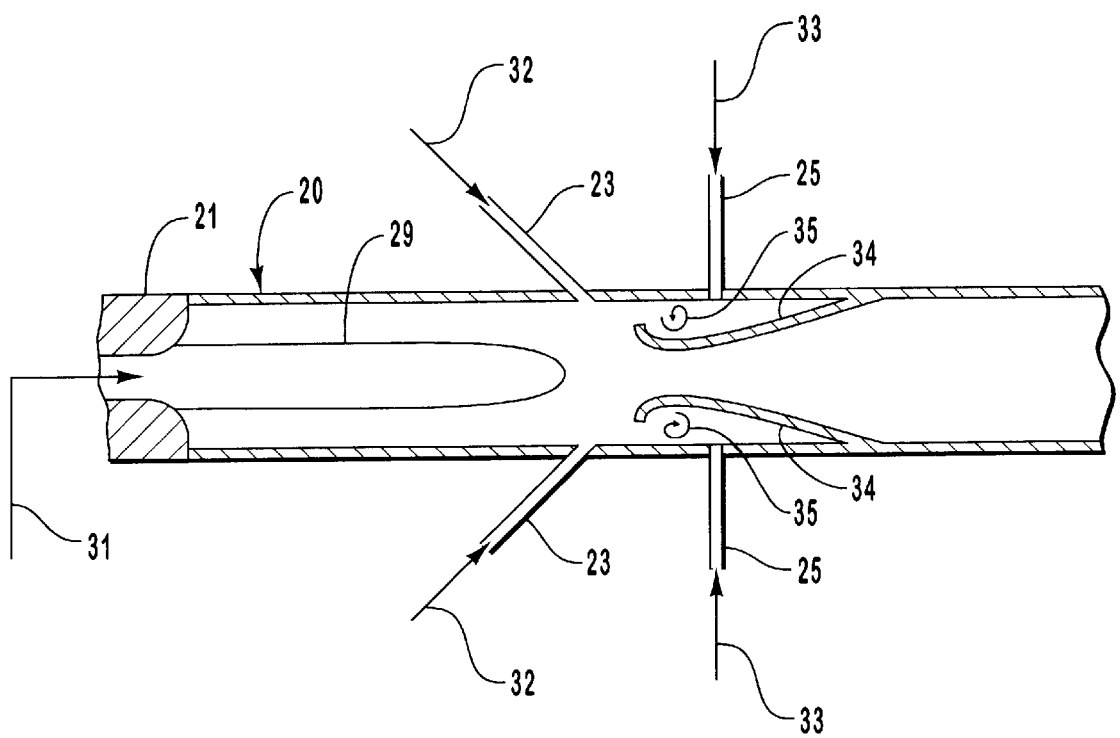
FIG. 9 illustrates side and top cross sectional views of a reaction chamber having a nozzle having two or more supply inlets.
Figure 9B:
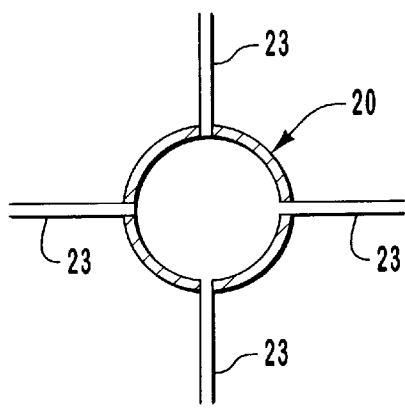

FIG. 9 shows a reactor chamber 20 having a virtual convergent-divergent nozzle. The chamber 20 has a plasma gas 31, plasma arc 21, and resulting plasma similar to FIG. 1. Supply inlets 23 focus the incoming reactant streams 32 so as force the reactants toward the center of the reactor chamber 20. The plasma gas 31 and reactant streams 32 as they come together produce an expansion of the reactant stream toward the outlet end of reaction chamber 23 to produce flow lines 34 with flow impedance 35. This expansion results in rapid cooling of the reactants. Supply inlets 25 allow reactant streams 33 containing for example a reducing gas, such as hydrogen, to prevent back reactions and enhance the virtual nozzle effect and the production of the desired product.

Figure 10:
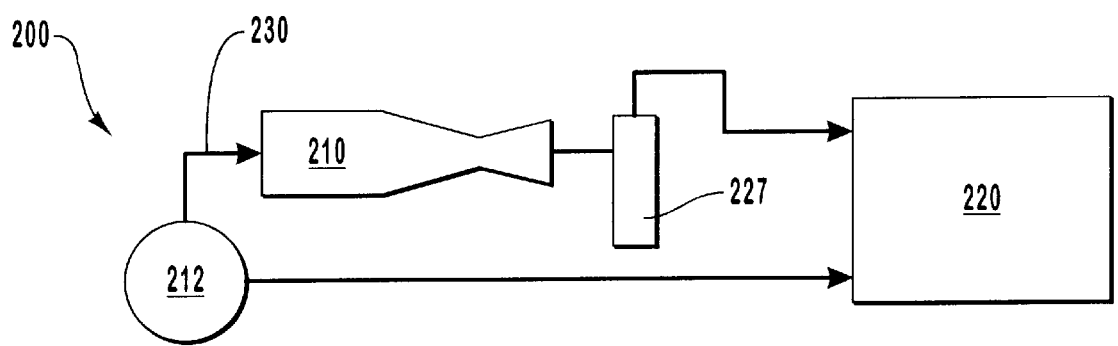
FIG. 10 illustrates the flow of an on-board plasma quench reformer system for natural gas fuel as part of a supplemental source of supplying combustible material to an internal combustion engine in addition to the natural gas.

FIG. 10 is an overview of an on-board system for an internal combustion engine that is powered by a hydrocarbon fuel such as natural gas. FIG. 10 demonstrates the supply of either liquid natural gas (LNG) or compressed natural gas (CNG) to an internal combustion engine 220.

FIG. 10 illustrates an on-board system 200 in which internal combustion engine 220 is supplied from a natural gas source 212. Vapors from natural gas source 212 are drawn off as reactants 230 to supply a fast quench reactor 210.

Where the fuel source is natural gas, a source of oxygen may be required in order to form carbon monoxide within fast quench reactor 210. Accordingly, air may be allowed to enter on-board system 200 as a source of oxygen. Alternatively carbon dioxide may be drawn from combustion gases of internal combustion engine 220.

Under certain conditions, the reaction product particles are collectible within a cycline separator shown generally at 227. Typical reaction product particles are carbon, carbon black, acetylene black, and the like. Where elemental carbon or rudimentary forms of carbon are removed from on-board system 200, the amount of carbon-containing emissions from internal combustion engine 220 is reduced.

It is preferable that the ratio of methane to carbon dioxide in the on-board system. For example, under preferred operating conditions, a 1:1 methane to carbon dioxide ratio provides carbon monoxide and hydrogen according to the following equation:

$$CO_2 + CH_4 \rightarrow 2CO + 2H_2.$$

Where methane is in excess, under preferred operating conditions, for example 1.1 moles methane to one mole carbon, excess hydrogen will be produced and a corresponding excess of elemental carbon according to the following equation:

$$CO_2 + 1.1CH_4 \rightarrow 2CO + 2.2H_2 + 0.2C.$$

The most preferred ratios of methane to carbon dioxide, not only for the on-board system but also for the plasma quench system as disclosed herein, is to have at least a 1:1 methane to carbon dioxide ratio. Where the methane to carbon dioxide ratio exceeds 1:1, as can be seen above, elemental carbon may be produced under the proper conditions as set forth herein. Thereby, the amount of carbon that is being supplied to an internal combustion engine, a fuel cell, or any other suitable heat engine, is being reduced. Consequently, the amount of green house gases ultimately emitted into the environment is reduced.

Where elemental carbon is being produced, it can be used as a supply source for the production of carbon monoxide by use of the inventive quenching apparatus disclosed herein. As set forth above, carbon may be reacted in the inventive apparatus in connection with carbon dioxide to form carbon monoxide. For both the on-board system and for the inventive plasma quench apparatus standing alone, carbon dioxide may be taken from a combustion process and combined with the elemental carbon to form carbon monoxide.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

We claim:

1. A method for thermally converting one or more carbon-containing reactants in a thermodynamically stable high temperature gaseous stream to at least one reaction product, comprising the following steps:

introducing a reactant stream that provides a source of carbon atoms and a source of oxygen atoms at one axial end of a reaction chamber containing an ionized gas, the reaction chamber comprising an inlet end and an outlet end;

heating the reactant stream in the reaction chamber to form a carbon monoxide containing reaction product stream;

the reaction chamber having a predetermined length sufficient to effect heating of the reactant stream to a temperature at which carbon monoxide is available as a reaction product stream at a location adjacent the outlet end of the reaction chamber;

expanding the reaction product stream through the outlet end of the reaction chamber to cool the gaseous stream by converting thermal energy to kinetic energy as the reaction product stream expands; and collecting the reaction product.

2. The method of claim 1, wherein the ionized gas is hydrogen.

3. The method of claim 1, the reactant stream further comprising methane.

4. The method of claim 1, wherein the reactant stream contains carbon dioxide.

5. The method of claim 1, the reactant stream further comprising methane and carbon dioxide.

6. The method of claim 1, the reactant stream further comprising methane and carbon dioxide in a methane to carbon dioxide ratio of about 1:1.

7. The method of claim 1, the reactant stream further comprising methane and carbon dioxide in a methane to carbon dioxide ratio of greater than 1:1.

8. The method of claim 1, wherein heating is accomplished by introducing a stream of plasma arc gas to a plasma torch at the one axial end of the reaction chamber to produce a plasma within the reaction chamber which extends toward its remaining axial end.

9. The method of claim 1, wherein cooling the reaction product is accomplished by use of a restrictive convergent-divergent nozzle.

10. The method of claim 1, wherein the reaction product includes a product ratio of about 0.3 mole carbon monoxide, to about 0.7 mole carbon dioxide, and the balance impurities.

11. The method of claim 1, wherein the reaction product includes a product ratio of about 0.7 mole carbon monoxide, to about 0.5 mole carbon dioxide, to about 0.1 mole diatomic hydrogen, to about 0.3 mole water, and the balance impurities.

12. The method of claim 1, wherein the reaction product includes a product ratio of about 1.2 mole carbon monoxide, to about 0.25 mole carbon dioxide, to about 0.5 mole diatomic hydrogen, to about 0.4 mole water, and the balance impurities.

13. The method of claim 1, wherein the reaction product includes a product ratio of about 1.5 mole carbon monoxide, to about 0.2 mole carbon dioxide, to about 0.9 mole diatomic hydrogen, to about 0.25 mole water, and the balance impurities.

14. The method of claim 1, wherein the reaction product includes a product ratio of about 1.75 mole carbon monoxide, to about 0.1 mole carbon dioxide, to about 1.5 mole diatomic hydrogen, to about 0.2 mole water, and the balance impurities.

15. A method for thermal conversion of a carbon atom source in a thermodynamically stable high temperature gaseous stream to carbon monoxide, comprising the following steps:

introducing a stream of plasma arc gas between the electrodes of a plasma torch including at least one pair of electrodes positioned at the inlet end of an axial reactor chamber, the stream of plasma arc gas being introduced at a selected plasma gas flow while the electrodes are subjected to a selected plasma input power level to produce a plasma within the reactor chamber and extending toward its outlet end;

thoroughly mixing an incoming reactant stream into the plasma by injecting at least a carbon atom source and an oxygen atom source into the reactor chamber at or adjacent to its inlet end at a selected injection angle and at a selected reactant input rate to progressively effect heat transfer between the plasma and the resulting gaseous stream as it flows axially toward the outlet end of the reactor chamber;

the length of the reactor chamber being sufficient to effect heating of the gaseous stream to a selected equilibrium temperature at which carbon monoxide end product is available as a thermodynamically unstable reaction product within the gaseous stream at a location adjacent to the outlet end of the reactor chamber;

directing the gaseous stream through a coaxial convergent-divergent nozzle positioned in the outlet end of the reactor chamber to rapidly cool the gaseous stream by converting thermal energy to kinetic energy as a result of adiabatic and isentropic expansion as it flows axially through the nozzle, the nozzle having a converging section and a diverging section respectively leading to and from a restrictive open throat; and cooling the gaseous stream exiting the nozzle by reducing its velocity while removing heat energy at a rate sufficient to prevent increases in its kinetic temperature.

16. A method for thermal conversion of a carbon atom source in a thermodynamically stable high temperature gaseous stream to carbon monoxide according to claim 15, wherein the carbon atom source comprises carbon dioxide.

17. A method for thermal conversion of a carbon atom source in a thermodynamically stable high temperature gaseous stream to carbon monoxide according to claim 15, wherein the carbon atom source includes a light hydrocarbon selected from the group consisting of methane, ethane, propane, and butane.

18. A method for thermal conversion of a carbon atom source in a thermodynamically stable high temperature gaseous stream to carbon monoxide according to claim 15, wherein the oxygen atom source is carbon dioxide.

19. A method for thermal conversion of a carbon atom source in a thermodynamically stable high temperature gaseous stream to carbon monoxide according to claim 15, wherein the oxygen atom source is air.

20. The method of claim 15, further comprising the following step:

accelerating the gaseous stream rapidly into the nozzle throat while maintaining laminar flow by passage of the gaseous stream through a converging section of the nozzle having an aspect ratio of about one half or smaller the diameter of the reactor chamber.

21. The method of claim 15, further comprising the following step:

controlling the residence time and reaction pressure of the gaseous stream in the reactor chamber by selection of the size of the restrictive open throat within the nozzle.

22. A method for thermal conversion of a carbon atom source in a thermodynamically stable high temperature gaseous stream to carbon monoxide according to claim 15, wherein the carbon atom source is carbon dioxide and methane in a molar ratio of about 1:1.

23. A method for thermal conversion of a carbon atom source in a thermodynamically stable high temperature gaseous stream to carbon monoxide according to claim 15, wherein the carbon atom source is carbon dioxide and methane in a molar ratio of more methane than carbon dioxide.

* * * * *